United States Patent
Horvath et al.

(10) Patent No.: US 12,201,588 B2
(45) Date of Patent: Jan. 21, 2025

(54) FULL SPECTRUM HEMP OIL COMPOSITIONS

(71) Applicant: Chemtor L.P., Lockhart, TX (US)

(72) Inventors: Andrew Horvath, Lockhart, TX (US); Ryan Raynaud, Lockhart, TX (US)

(73) Assignee: Chemtor L.P., Lockhart, TX (US)

( * ) Notice: Subject to any disclaimer, the term of this patent is extended or adjusted under 35 U.S.C. 154(b) by 58 days.

(21) Appl. No.: 17/489,255

(22) Filed: Sep. 29, 2021

(65) Prior Publication Data

US 2023/0097799 A1    Mar. 30, 2023

(51) Int. Cl.

| | | |
|---|---|---|
| A61K 31/05 | (2006.01) | |
| A23L 2/52 | (2006.01) | |
| A23L 33/105 | (2016.01) | |
| A61K 9/107 | (2006.01) | |
| A61K 31/015 | (2006.01) | |
| A61K 31/352 | (2006.01) | |
| A61K 36/185 | (2006.01) | |

(52) U.S. Cl.
CPC ............ *A61K 31/05* (2013.01); *A23L 2/52* (2013.01); *A23L 33/105* (2016.08); *A61K 9/1075* (2013.01); *A61K 31/015* (2013.01); *A61K 31/352* (2013.01); *A61K 36/185* (2013.01); *A23V 2002/00* (2013.01)

(58) Field of Classification Search
CPC .................................................... A61K 31/05
See application file for complete search history.

(56) References Cited

U.S. PATENT DOCUMENTS

| | | | |
|---|---|---|---|
| 10,738,268 B2 | 8/2020 | Leo | |
| 10,993,977 B2 * | 5/2021 | Jansen | ............... B01D 15/1828 |
| 11,648,219 B2 * | 5/2023 | Horvath | ................ A61K 9/006 |
| | | | 514/568 |
| 2021/0030824 A1 | 2/2021 | Jansen et al. | |

FOREIGN PATENT DOCUMENTS

| | | |
|---|---|---|
| WO | WO2021154719 A1 | 8/2021 |
| WO | WO2023056262 A1 | 4/2023 |
| WO | WO-2020028992 A1 * | 5/2023 ............ A61K 31/05 |

OTHER PUBLICATIONS

"Material Safety Data Sheet", Sigma-Aldrich, Sep. 12, 2011 (Year: 2011).*
Schaforth et al., "9-cis-Tetrahydrocannabinol: Natural Occurrence, Chirality, and Pharmacology", Journal of Natural Product, pp. 2502-2510, Jul. 25, 2021 (Year: 2021).*
Axiomm Technologies, "What is nano THC? How nanoemulsions create new cannabis building blocks", Leafly, Jul. 28, 2020 (Year: 2020).*
Partial International Search Report and Written Opinion dated Nov. 2, 2022, PCT/US2022/077114 filed on Sep. 27, 2022.
International Search Report and Written Opinion dated Feb. 2, 2023, PCT/US2022/077114 filed on Sep. 27, 2022.
International Preliminary Report on Patentability dated Apr. 11, 2023, PCT/US2022/077114 filed on Sep. 27, 2022.

* cited by examiner

*Primary Examiner* — Andrew D Kosar
*Assistant Examiner* — Gillian A Hutter
(74) *Attorney, Agent, or Firm* — Conley Rose, P.C.

(57) ABSTRACT

A composition comprising a cannabidiol at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof; and a terpene. A nanoemulsion comprising a cannabidiol; a terpene; and an aqueous fluid, wherein the cannabidiol and terpene are in an emulsion in the aqueous fluid. A full spectrum hemp oil composition comprising at least one stereoisomer of tetrahydrocannabinol; cannabinodiol; and at least one cannabinoid selected from the group consisting of cannabichromenes, cannabicyclols, cannabidiols, cannabielsoins, cannabigerols, cannabinols, cannabinodiols, cannabitriols, and a combination thereof.

26 Claims, 3 Drawing Sheets

FULL SPECTRUM HEMP OIL COMPOSITIONS

FIELD

The present disclosure relates generally to therapeutic compositions. More particularly, the present disclosure relates to phytocannabinoid compositions SUMMARY Disclosed herein is a composition comprising a cannabidiol and at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof, and a terpene.

Also disclosed herein is a nanoemulsion comprising a cannabidiol; a terpene; and an aqueous fluid, wherein the cannabidiol and terpene are in an emulsion in the aqueous fluid.

Also disclosed herein is a full spectrum hemp oil composition comprising at least one stereoisomer of tetrahydrocannabinol; cannabinodiol; and at least one cannabinoid selected from the group consisting of cannabichromenes, cannabicyclols, cannabidiols, cannabielsoins, cannabigerols, cannabinols, cannabinodiols, cannabitriols, and a combination thereof.

BRIEF DESCRIPTION OF DRAWINGS

For a detailed description of the aspects of the disclosed processes and systems, reference will now be made to the accompanying drawings in which.

BACKGROUND

Industrial hemp or hemp production has recently been the subject of increasing interest around the world, especially in the United States. Hemp is a dioecious annual wind-pollinated crop with separate male and female plants, and occasionally monoecious. It is also a short-day and photoperiod sensitive crop. Hemp is a specific type of *cannabis* known scientifically as *Cannabis sativa* L. Though they are both parts of the same family, hemp and marijuana have differing chemistries and characteristics. In particular, the plants differ in their cannabinoid and terpene content and distribution.

Figure 1:
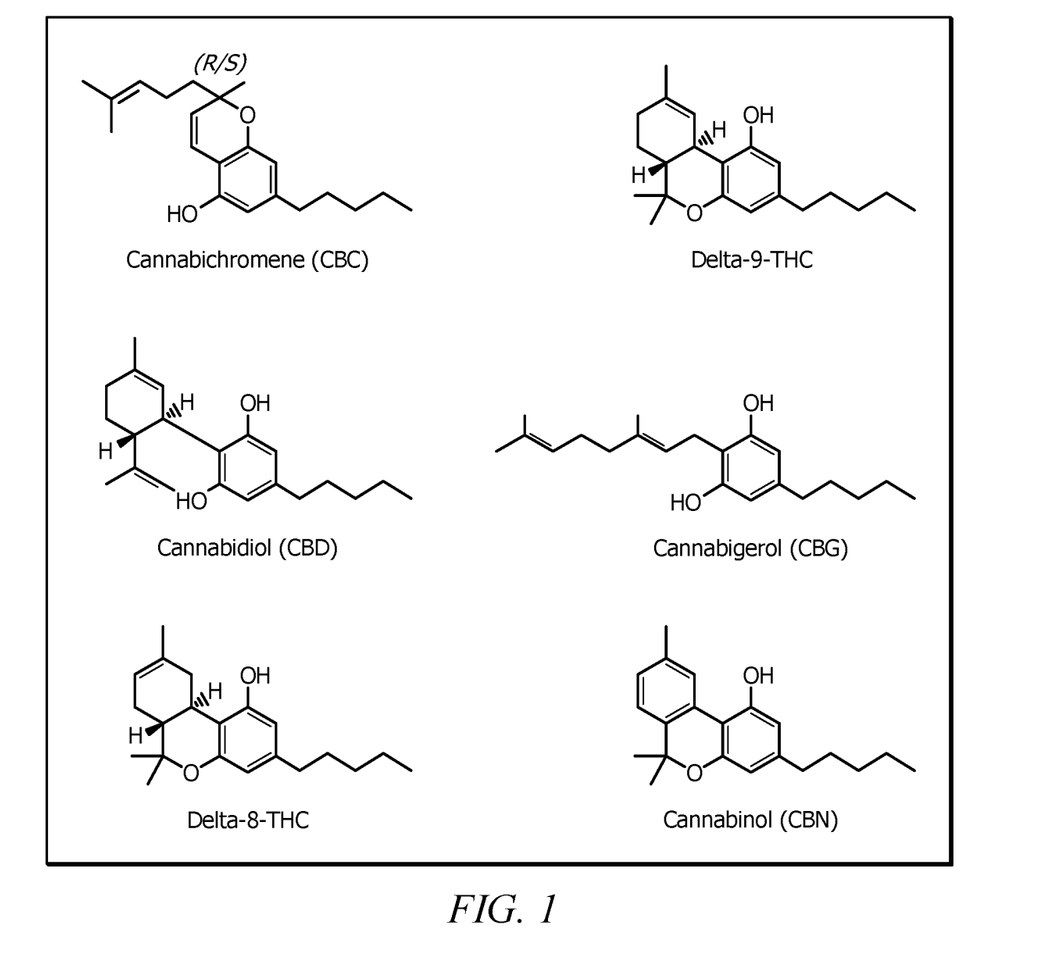
FIG. 1 depicts structures of cannabinoids.

Cannabinoids are a class of diverse chemical compounds that interact with cannabinoid receptors on cells that modulate physiological responses in the brain, peripheral nervous and immune systems. The structure of several cannabinoids is presented in FIG. 1. The native endocannabinoid ligands (produced naturally in the body by humans and animals), the phytocannabinoids (found in some plants), and synthetic cannabinoids (manufactured chemically) bind to receptors throughout the body and control downstream signal transduction. Cannabinoids such as cannabidiol (CBD), cannabigerol (CBG), cannabichromene (CBC), and cannabigerivarin (CBGV) are the major constituents in hemp and hemp extracts while psychoactive compounds such as Δ9-tetrahydrocannabinol (THC) are minor components. Cannabinoids have demonstrated the potential to be used in clinical applications in a variety of medical conditions such as for the treatment of epilepsy and other motor disorders, inflammation, mood and anxiety disorders, sleep dysfunction and eating disorders. For example, CBD is considered a promising antineoplastic agent on the basis of its in vitro and in vivo activity against tumor cells.

Similarly, hemp contains a number of terpenes that are the basic elements in essential oils and are frequently used in food additives, perfumery, and aromatherapy. The medicinal properties of terpenes in correlation to various health issues is an active research area.

DETAILED DESCRIPTION

Disclosed herein are methods for the production of a full-spectrum composition (FSC) derived from a biomass such as the hemp plant. In an aspect, the FSC comprises (i) one or more cannabinoids and (ii) one or more terpenes. In another aspect, the FSC comprises at least two cannabinoids. In yet another aspect, an FSC of the present disclosure excludes terpenes.

As described above, hemp and marijuana can be discriminated from one another by various aspects of their chemistry including their level of THCA or Δ9-THC. Hemp is legally classified as originating from the *Cannabis sativa* plant, where the level of Δ9-THC in the plant is confirmed to be less than 0.3% on a dry weight basis in the plant. Any plant that does not meet this definition is considered "Marijuana". In general, marijuana is the preferred option for customers looking for Δ9-THC, and hemp is the preferred option for CBD.

Once a plant has legally been determined to be "hemp", the plant flower and trim is often processed to extract the hemp oil, with the end goal being the isolation of the plant cannabinoids and terpenes. The referenced "hemp oil" is different from hemp seed oil in that hemp oil is very rich in cannabinoids and terpenes, where the hemp seed oil has no cannabinoids.

As described in more detail herein, the extraction of the hemp oil and terpenes can start with various extraction methods such as supercritical $CO_2$, cryo-ethanol, and the like. This crude extract can comprise between about 40 weight percent (wt. %) to 65 wt. % cannabinoids, with the balance being terpenes, chlorophyll, carbohydrates, gums, plant matter, etc. The next step in the refining process is commonly a short-path distillation that separates the residual extraction solvent from the terpenes from the cannabinoids from the residual higher molecular weight residual pitch. The product of the short-path distillation process can be referred to as a "Full Spectrum Distillate", where the material can comprise from 50 wt. % to 85 wt. % cannabinoids based on the total weight of the Full Spectrum Distillate. In an aspect, 95% of the cannabinoids in the Full Spectrum Distillate are CBD.

In some aspects, the Full Spectrum Distillate has a higher cannabinoid content. However, there are 113 known cannabinoid species, and the normal analytical methods only include 10-20 species for quantification, which can then underrepresent the cannabinoid content in the composition. These "Minor Cannabinoids" are greatly valued by customers of hemp oil, because of the perceived value in something known as the "entourage effect".

The entourage effect is the physiological benefit of ingesting a full plant extract, to include all cannabinoids and terpenes found in the plant. From a physiological perspective, plant derived cannabinoids (phyto cannabinoids) will interact with an animal's endocannabinoid system to produce a physiological response. To date, humans have been confirmed to have 2 types of receptors activated by such cannabinoids, or the feedback-response signaling system associated with the endocannabinoid system. Of note, the terpene β-caryophyllene is also a functional phytocannabinoid that is known to bind to the human CB2 receptor.

After the short-path distillation process, a subsequent manufacturing process can involve the isolation of CBD as a crystalline powder. The manufacturing process for "CBD isolate" can involve dissolving the full spectrum distillate in a solvent, then slowing modifying the solvent level and temperature to cause the highly concentrated levels of CBD to precipitate from solution as a combination of crystallized CBD and an amorphous CBD rich powder. This "CBD isolate" is of a very high purity, for example having a greater than 99.5 wt. % pure CBD. The other cannabinoids from the full spectrum distillate remain in the Isolate solvent in an intermediate product known as "Mother Liquor".

Plants that meet the legal definition of "Hemp" tend to have a very high concentration of CBD, with minimal THC, CBG, CBDV, CBN, etc. Plants that have been bred for the medical marijuana market tend to have a very high level of THC, with minimal CBD, or other minor cannabinoids. For customers interested in the entourage effect associated with the minor cannabinoids from Hemp, the Mother Liquor from the CBD isolation process represents a rich repository of concentrated minors. In order to be a "Balanced Full Spectrum Hemp Product", the Mother Liquor can be supplemented with some CBD, and at least a portion of the terpenes that were eliminated during the short-path process can be re-introduced.

While there are many techniques that have been developed for the consumption of hemp derivatives, an emerging technology of high interest is the use of specialized emulsifiers and surfactants, and mixers or ultrasonic mixers (sonicators) that can be used to produce a "nano-emulsion" of hemp oil in an aqueous continuous phase. The benefits of these "nano-emulsions is improved clarity of the mixture, improved shelf stability of the emulsion, and improved bio-availability of the emulsified oil.

As disclosed herein, a product of the present disclosure can be a dilute form of a nano-emulsified full spectrum hemp oil, where the final product meets the legal limits for the amount of Δ9-THC (e.g., below the level qualifying as a marijuana product) that can be present in the final composition. One consideration of this formulation is that the amount of Δ9-THC is less than 0.3 wt. % of the final composition. As an example, a typical can of soda contains a volume of 12 fluid ounces, or 355 mL. A dilute form of the proposed nano-emulsion can contain approximately 350 grams of product. With the legal limit on THC being 0.3%, the maximum amount of THC that could be contained in the final dilution in order to be below the legal THC limit is estimated to be 1,050 mg of Δ9-THC. A second aqueous based, carbohydrate rich example to consider is the incorporation of the Hemp Oil into honey through the use of a surfactant, such as sunflower lecithin. A third example to consider is the use of a lipid rich diluent, such as peanut butter, butter, margarine, or cheese.

The final FSC can comprise one or more cannabidiols and one or more terpenes. In some aspects, the resulting FSC can comprise one or more cannabidiols including any of those extracted from hemp. For example, an FSC of the present disclosure comprises one or more cannabinoids selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols and a combination thereof. Nonlimiting examples of cannabinoids that may be present in the FSCC include cannabichromene (CBC), cannabichromenic acid (CBCA), cannabichromevarin (CBCV), cannabichromevarinic acid (CBCVA), cannabicyclol (CBL), cannabicyclolic acid (CBLA), cannabicyclovarin (CBLV), cannabidiol (CBD), cannabidiol monomethylether (CBDM), cannabidiolic acid (CBDA), cannabidiorcol (CBD-C1), cannabidivarin (CBDV), cannabidivarinic acid (CBDVA), cannabielsoic acid B (CBEA-B), cannabielsoin (CBE), cannabielsoin acid A (CBEA-A), cannabigerol (CBG), cannabigerol monomethylether (CBGM), cannabigerolic acid (CBGA), cannabigerolic acid monomethylether (CBGAM), cannabigerovarin (CBGV), cannabigerovarinic acid (CBGVA), cannabinodiol (CBND), cannabinodivarin (CBVD), cannabinol (CBN), cannabinol methylether (CBNM), cannabinol-C2 (CBN-C2), cannabinol-C4 (CBN-C4), cannabinolic acid (CBNA), cannabiorcool (CBN-C1), cannabivarin (CBV), 10-ethoxy-9-hydroxy-delta-6a-tetrahydrocannabinol, 8,9-dihydroxy-delta-6a-tetrahydrocannabinol, cannabitriol (CBT), cannabitriolvarin (CBTV), delta-8-tetrahydrocannabinol (Δ8-THC), delta-8-tetrahydrocannabinolic acid (Δ8-THCA), delta-9-tetrahydrocannabinol (Δ9-THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THCV), delta-9-tetrahydrocannabivarinic acid (THCVA), 10-oxo-delta-6a-tetrahydrocannabinol (OTHC), cannabichromanon (CBCF), cannabifuran (CBF), cannabiglendol, cannabiripsol (CBR), cannbicitran (CBT), dehydrocannabifuran (DCBF), delta-9-cis-tetrahydrocannabinol (cis-THC), trihydroxy-delta-9-tetrahydrocannabinol (triOH-THC) or a combination thereof.

Figure 2:
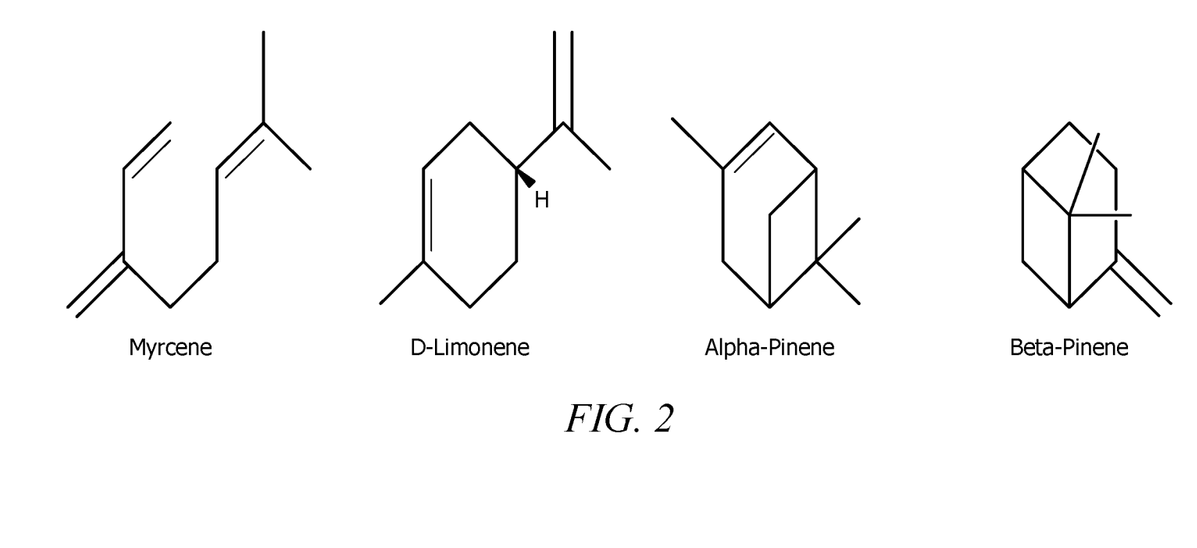
FIG. 2 depicts structures of terpenes.

In an aspect, the FSC comprises one or more terpenes. Terpenes refer to a class of natural products consisting of compounds with the general formula $(C_5H_8)_n$. In an aspect, a terpene that may be present in the FSC has the formula $(C_5H_8)_n$ where n ranges from 1 to 20, alternatively n ranges from 1 to 10 or alternatively n ranges from 1 to 5. Terpenes are unsaturated hydrocarbons that can be produced predominantly by plants and are further classified by the number of carbons present in the terpene such that monoterpenes are $C_{10}$ compounds, sesquiterpenes ($C_{15}$), diterpenes ($C_{20}$), triterpenes ($C_{30}$), etc. In an aspect, the FSC comprises D-limonene, β-caryophyllene, myrcene, linalool, α-pinene, nerolidol, humulene, α-bisabolol, camphene, 3-carene, citronellol, cymene, eucalyptol, farnesene, fenchol, geraniol, guaiol, isopropyltoluene, isopulegol, nerolidol, α-ocimene, α-terpinene, γ-terpinene, terpinolene, and a combination thereof. The structures of several terpenes commonly found in Hemp plant are shown in FIG. 2.

Disclosed herein is a method of isolation an FSC from hemp plant material. In one or more aspects, the hemp plant material is processed to facilitate removal of the target compounds from the plant. For example, the hemp plant material may be dried, if it is not already provided in dried form. For example, the hemp plant material may be dried in a dry room with a dehumidifier air controller, or it may be flash dried in a vacuum oven at a pressure of less than about 2 kPa. In an aspect, using any suitable methodology, the hemp plant material may be subjected to drying under conditions sufficient to reduce the moisture content of the hemp plant material to less than about 10 wt. % based on the total weight of the hemp plant material. Alternatively, the moisture level is reduced to less than about 8 wt. % or alternatively less than about 5 wt. %. The temperature of the oven and the drying time depend on the moisture level of the hemp plant material and may be measured using a moisture analyzer. In some aspects, a hygrometer may be used to measure the moisture content of the hemp plant materials. Subsequent to drying, the hemp plant material may be ground, for example to an average size between 250 μm to about 500 μm. Any suitable technique, such as a mill or blender, may be used for grinding of the hemp plant materials. In an alternative aspect, grinding of the hemp plant material may take place before the drying of the hemp plant material.

Figure 3:
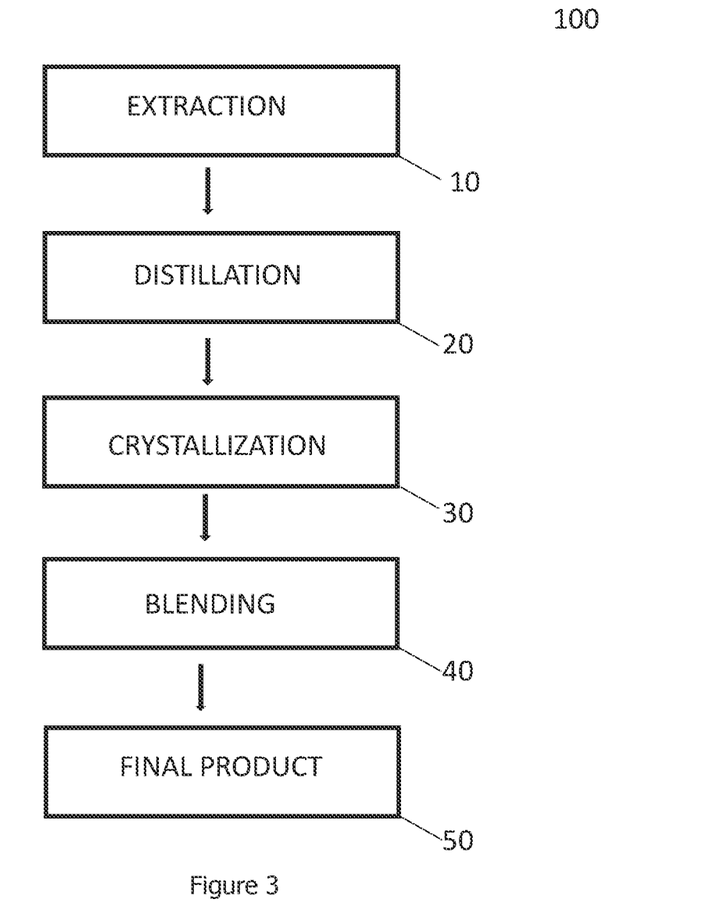
FIG. 3 is a process flow diagram of an aspect of methods disclosed herein.

In an aspect, a method for the production of an FSC begins with the isolation of a series of target compounds from the hemp plant. Herein the target compounds refer to one or more cannabinoids and one or more terpenes present in the hemp plant material. A method for isolation of the target compounds is shown in FIG. 3. FIG. 3 is a process flow diagram 100 of a method for the isolation of the target compounds comprising the steps of extraction 10, distillation 20, concentration 30 and blending 40 to achieve the final product 50. In one or more aspects, the final product, 50, comprises the target compounds and is utilized as the FSC. In other aspects, the final product, 50, comprises the target compounds which are further processed and subsequently utilized as the FSC.

In an aspect, a method of obtaining an FSC begins with extraction of hemp oil from the hemp plant material. Specifically, the hemp plant material, which refers to the plant flower and trim in some contexts, is often processed to extract the hemp oil, with the end goal being the isolation of the plant cannabinoids and terpenes. Herein reference is made to "hemp oil" which contains the cannabinoids and terpenes. As noted herein, the hemp oil is different than hemp seed oil, which has little to no cannabinoids.

Extraction of the hemp plant material may be carried out using any suitable methodology. For example, solvent extraction can be used to extract the components of the hemp plant material. For example, extraction of the hemp plant material may be carried using carbon dioxide ($CO_2$) extraction (e.g., supercritical $CO_2$ extraction, etc.). Extraction of the hemp plant material with $CO_2$ uses the gas in its normal state as well as in supercritical liquid form. The supercritical liquid form of $CO_2$ is obtained through the use of a pressurized chamber, called a closed-loop extractor in which $CO_2$ gas is compressed until it becomes a liquid. Contacting of the $CO_2$ liquid with the hemp plant material under the disclosed conditions results in extraction of soluble compounds such as the target compounds from the plant. In an aspect, the mixture of liquid $CO_2$ and hemp plant is brought back to temperatures and pressures at which the $CO_2$ reverts to gas and evaporates, leaving behind a crude extract and the extracted hemp plant.

In an alternative aspect, extraction of the hemp plant may be carried using a solvent. Nonlimiting examples of solvents suitable for use in extraction of the hemp plant material include organic solvents such as ethanol, butanes, heptanes, benzene, toluene, and/or propane. In solvent extraction, the method typically involves immersion of the biomass (i.e., hemp plant material) in a solvent media to provide effective mass transfer for a given period. Solvent extraction is a generic term referring to all methods conventionally used for extraction purposes, which includes the use of different machines in batch, semi-batch or continuous form to provide the required contact between solvent and hemp plant material in any scale. The solvent extraction can take place in various reactor such as stirred tank reactors, packed bed reactors (e.g., with the hemp plant material forming the packed bed), fluidized bed reactors, or the like.

Subsequent to extraction, a mixture containing the extracted hemp plant and a crude extract comprising the target compounds can be obtained. In one or more aspects, the crude extract comprises from about 40 wt. % to about 65 wt. % cannabinoids based on the total weight of the crude extract with the remainder of the crude extract comprising terpenes, chlorophyll, carbohydrates, gums and plant matter.

In an aspect, a method of obtaining an FSC further comprises separation of the crude extract. In some aspects, the separation can comprise distillation, 20, of the crude extract. Distillation may be carried out using any suitable methodology. For example, distillation may be carried out using any distillation device or technique, including for example, without limitation, short path distillation, thin film distillation, wiped film distillation, and spinning band distillation. Distillation may be performed under vacuum or without vacuum. In an aspect, the distillation is a short path distillation. Herein short path distillation refers to the molecular separation of unique compounds through a process of slow thermal heating. Each target compound in the hemp plant material (e.g., CBD, β-carophyllene, etc.) has a different vapor pressure point or boiling point. The vapor pressure temperature is unique for each cannabinoid, terpene and any other chemical compounds thereby allowing for a separation between the various components of the crude extract.

The crude extract, once distilled, separates the residual extraction solvent separated from the terpenes, cannabinoids and residual higher molecular weight residual pitch. The product of the short-path distillation process can be referred to as a "Full Spectrum Distillate" (FSD). In an aspect, the FSD comprises from about 75 wt. % to about 85 wt. % cannabinoids based on the total weight of the FSD. In an aspect, CBD comprises about 95 wt. % of the cannabinoids present in the FSD.

In an aspect, the FSD can be optionally further concentrated to form a crystalline powder, which can be termed an isolate. Any suitable methodology for the concentration of FSD to form an isolate may be employed. For example, a method of forming the isolate can comprise dissolving, via an agitated vessel, the FSD and a solvent to thereby form a slurry. The method may further comprise heating, via a jacket of the agitated vessel, the slurry to reach a dissolving temperature whereby the FSD dissolves in the solvent. Subsequently, the heated slurry may be cooled via a jacket of the agitated vessel to reach a crystallization temperature whereby the FSD forms a precipitant, the isolate. The precipitant may be dried under any suitable conditions to form a dried isolate. In some aspects prior to the drying, the isolate can be washed with a washing solvent (e.g., pentanes).

In another aspect, formation of the isolate comprises dissolution of the Full Spectrum Distillate in a solvent. The solvent level and temperature may then be slowly modified to cause the highly concentrated levels of CBD to precipitate from solution as a combination of crystallized CBD and an amorphous CBD rich powder. In an aspect, the isolate comprises equal to or greater than about 95 wt. %, greater than about 96 wt. %, greater than about 97 wt. %, greater than about 98 wt. %, or greater than about 99 wt. % CBD based on the total weight of the isolate.

In an aspect, other cannabinoids from the FSD remain in the solvent. The solvent containing the minor cannabinoids (e.g., CBG, CBC, d9-THC) which have been concentrated is termed the "Mother Liquor."

In an aspect, the Mother Liquor may be used to produce the FSC. For example, a portion of the mother liquor may be blended with a portion of the isolate to produce a material having some user-desired level of a plurality of cannabinoids and terpenes (e.g., the FSC). The amounts and degree of mixing can be selected to provide a desired ratio of individual cannabinoids to other cannabinoids, or the cannabinoids to the terpenes as described in more detail herein. In some aspects, the ratio of specific cannabinoids to other specific cannabinoids, or the ratio of the cannabinoids to the terpenes in the FSC may differ from the initial ratio of specific cannabinoids to other specific cannabinoids or the cannabinoids to the terpenes in the biomass.

In some aspects, the mother liquor can be processed to isolate one or more discrete cannabinoids prior to blending any of the cannabinoids to form the FSC. Various separation techniques including chromatographic separation techniques can be used to separate the mother liquor into discrete components, which may then be present in a solvent or carrier fluid. The solvent or carrier can be removed to isolate the discrete components. The individual components or specific cannabinoids can then be used in the blends to form the FSC as described herein.

In an aspect, the FSC can comprise one or more additional components. In some aspects, the FSC can be treated to form an emulsion, and additives such as specialized emulsifiers, surfactants, and other components (e.g., lecithin such as Sunflower Lecithin) can be added to form the emulsion. The mixture can pass through one or more mixers or blenders such as paddle mixers, or ultrasonic mixers (e.g., sonicators) to produce a "nano-emulsion" of the FSC, where the Full Spectrum Distillate or the Full Spectrum Distillate blend (oleaginous phase) is suspended in an aqueous continuous phase. Nonlimiting examples of emulsifiers or surfactants suitable for use in the FSC nanoemulsions include agar, albumin, alginates, casein, ceatyl alcohol, cholic acid, desoxycholic acid, diacetyl tartaric acid esters, egg yolk, glycerol, gums, carrageenan, lecithin, monoglycerides, diglycerides, monosodium phosphate, monostearate, propylene glycol, aurocholic acid, salts thereof of or a combination thereof. Nanoemulsions of the FSC advantageously provide an improved clarity of the mixture, improved shelf stability of the emulsion, and improved bio-availability of the emulsified oil.

The FSC can have a variety of formulations based on the amount of the mother liquor mixed with the isolate and/or other additives or final solvents. The use of the process described herein can allow for specific amounts of the cannabidiols and terpenes to be achieved in a unique formulation that may not be obtained through simple separation techniques alone. Specific examples of formulations can include, but are not limited to:

In an aspect, an FSC of the present disclosure consists essentially of a single stereoisomer of THC (d8-, d9-, d10) and CBD where the level of d9-THC in the final product is less than 0.3 wt. % based on the weight of the final product.

In an aspect, an FSC of the present disclosure comprises at least one stereoisomer of THC (d8-, d9-, d10-), CBD and at least one other cannabinoid where the level of d9-THC in the final product is less than 0.3 wt. % based on the weight of the final product.

In an aspect, an FSC of the present disclosure comprises at least one stereoisomer of THC (d8-, d9-, d10-), CBD and at least one other cannabinoid where the ratio of THC to CBD ranges from about 0.9:1.0 to about 1.1:1.0 or alternatively from about 1.0:0.9 to about 1.0:1.1.

In an aspect, an FSC of the present disclosure comprises at least one stereoisomer of THC (d8-, d9-, d10-), CBD and at least one other cannabinoid, where the ratio of concentration of THC:CBD ranges from about 1.8:1 to about 2.2:1.

In an aspect, an FSC of the present disclosure is a water-soluble nanoemulsion having an oleaginous phase comprising from about 0 to about 85 wt. % d9-THC, from about 0 to about 85 wt. % CBD, from about 0 to about 50 wt. % of another cannabinoid, and from about 0 to about 25 wt. % terpenes based on the total weight of the nanoemulsion.

In an aspect, an FSC of the present disclosure is a water-soluble nanoemulsion having from about 1 wt. % to about 15 wt. % water soluble terpenes based on the total weight of the nanoemulsion.

In an aspect, the FSC nanoemulsion is included in an ingestible or edible product. Herein "edible" refers to a material that is fit to be eaten as food. "Food" herein refers to any edible product intended for consumption by humans or animals. The term "food" and the term "food and beverage" are used herein interchangeably. In one or more aspects, the final product contains an amount of d9-THC in the final composition that meets the legal limit. In an aspect, the FSC is included in the ingestible or edible product in an amount that results in an amount of d9-THC of less than about 0.3% of the final composition. For example, a typical can of soda contains a volume of 12 fluid ounces, or 355 mL. In such aspects, a dilute form of the FSC nanoemulsion may contain approximately 350 grams of product. With the legal limit on THC being 0.3 wt. %, the maximum amount of THC that could be preset in the typical can of soda is estimated to be 1,050 mg of d9-THC.

Examples of food and beverage products or formulations to which a FSC or FSC nanoemulsion can be introduced include, but are not limited to sweet coatings, frostings, or glazes for comestible products or any entity included in the Soup category, the Dehydrated and Culinary Food Category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, the Sauces, Dressings, Condiments category, the Spreads category or combinations thereof.

In an aspect, a FSC is included in a non-edible ingestible product. Herein, "non-edible products" refer to supplements, nutraceuticals, functional food products (e.g., any fresh or processed food claimed to have a health-promoting and/or disease-preventing properties beyond the basic nutritional function of supplying nutrients), pharmaceutical and over the counter products. In general, an over the counter (OTC) product generally refers to a product for household and/or personal use which may be sold without a prescription and/or without a visit to a medical professional. In an aspect, the FSC or FSC nanoemulsion is included in a beverage.

EXAMPLES

The presently disclosed subject matter having been generally described, the following examples are given as particular aspects of the subject matter and to demonstrate the practice and advantages thereof. It is understood that the examples are given by way of illustration and are not intended to limit the specification or the claims in any manner.

EXAMPLE

A product of the present disclosure contains water-infused with emulsified or nano-emulsified cannabinoid oil, seltzer water so infused, soda water so infused, honey, chocolate, butter based desert materials (e.g., Rice crispy treats, fruity pebble treats), queso, peanut butter, peanut brittle, gummy bears and other "gummy" products, including gelatin or pectin based gummies.

ADDITIONAL DISCLOSURE

The following are non-limiting, specific embodiments in accordance and with the present disclosure:

A first aspect which is a composition comprising a cannabidiol; at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof, and a terpene.

The second aspect which is the composition of the first aspect wherein the at least one compound comprises cannabichromene (CBC), cannabichromenic acid (CBCA), cannabichromevarin (CBCV), cannabichromevarinic acid (CBCVA), cannabicyclol (CBL), cannabicyclolic acid (CBLA), cannabicyclovarin (CBLV), cannabidiol (CBD), cannabidiol monomethylether (CBDM), cannabidiolic acid (CBDA), cannabidiorcol (CBD-C1), cannabidivarin (CBDV), cannabidivarinic acid (CBDVA), cannabielsoic acid B (CBEA-B), cannabielsoin (CBE), cannabielsoin acid A (CBEA-A), cannabigerol (CBG), cannabigerol monomethylether (CBGM), cannabigerolic acid (CBGA), cannabigerolic acid monomethylether (CBGAM), cannabigerovarin (CBGV), cannabigerovarinic acid (CBGVA), cannabinodiol (CBND), cannabinodivarin (CBVD), cannabinol (CBN), cannabinol methylether (CBNM), cannabinol-C2 (CBN-C2), cannabinol-C4 (CBN-C4), cannabinolic acid (CBNA), cannabiorcool (CBN-C1), cannabivarin (CBV), 10-ethoxy-9-hydroxy-delta-6a-tetrahydrocannabinol, 8,9-dihydroxy-delta-6a-tetrahydrocannabinol, cannabitriol (CBT), cannabitriolvarin (CBTV), delta-8-tetrahydrocannabinol (Δ8-THC), delta-8-tetrahydrocannabinolic acid (Δ8-THCA), delta-9-tetrahydrocannabinol (Δ9-THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THCV), delta-9-tetrahydrocannabivarinic acid (THCVA), 10-oxo-delta-6a-tetrahydrocannabinol (OTHC), cannabichromanon (CBCF), cannabifuran (CBF), cannabiglendol, cannabiripsol (CBR), cannbicitran (CBT), dehydrocannabifuran (DCBF), delta-9-cis-tetrahydrocannabinol (cis-THC), trihydroxy-delta-9-tetrahydrocannabinol (triOH-THC) or a combination thereof.

A third aspect which is the composition of any of the first through second aspects wherein terpene comprises monoterpenes ($C_{10}$), sesquiterpenes ($C_{15}$), diterpenes ($C_{20}$), triterpenes ($C_{30}$) or a combination thereof.

A fourth aspect which is the composition of any of the first through third aspects wherein the terpene comprises D-limonene, β-carophyllene, myrcene, linalool, α-pinene, nerolidol, humulene, α-bisabolol, camphene, 3-carene, citronellol, cymene, eucalyptol, farnesene, fenchol, geraniol, guaiol, isopropyltoluene, isopulegol, nerolidol, α-ocimene, α-terpinene, γ-terpinene, terpinolene, or a combination thereof.

A fifth aspect which is the composition of any of the first through fourth aspects wherein the cannabidiol is an isolate.

A sixth aspect which is the composition of any of the first through fifth aspects wherein the terpene is a component of a mother liquor.

A seventh aspect which is the composition of any of the first through sixth aspects wherein the at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols and a combination thereof is a component of the mother liquor.

An eighth aspect which is the composition of any of the first through seventh aspects wherein the at least one compound comprises delta-9-tetrahydrocannabinol.

A ninth aspect which is the composition of any of the first through eighth aspects wherein the at least one compound comprises cannabigerol.

A tenth aspect which is a nanoemulsion comprising a cannabidiol; a terpene; and an aqueous fluid, wherein the cannabidiol and terpene are in an emulsion in the aqueous fluid.

An eleventh aspect which is the nanoemulsion of the tenth aspect further comprising at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof, and A twelfth aspect which is the nanoemulsion of any of the tenth through eleventh aspects further comprising delta-9-tetrahydrocannabinol.

A thirteenth aspect which is the nanoemulsion of the twelfth embodiment wherein the nanoemulsion is an edible product comprising an amount of delta-9-tetrahydrocannabinol of less than about 0.3 wt. % based on the total weight of the edible product.

A fourteenth aspect which is the nanoemulsion of any of the twelfth through thirteenth aspects wherein the edible product is a beverage.

A fifteenth aspect which is a full spectrum hemp oil composition comprising at least one stereoisomer of tetrahydrocannabinol; cannabinodiol; and at least one cannabinoid selected from the group consisting of cannabichromenes, cannabicyclols, cannabidiols, cannabielsoins, cannabigerols, cannabinols, cannabinodiols, cannabitriols, and a combination thereof.

A sixteenth aspect which is the composition of the fifteenth aspect wherein the at least one stereoisomer of tetrahydrocannabinol comprises less than 0.3 wt. % of the composition.

A seventeenth aspect which is the composition of the fifteenth through the sixteenth aspects wherein the amount of THC:CBD ranges from about 0.9:1.0 to about 1.1:1.0.

An eighteenth aspect which is the composition of the fifteenth through sixteenth aspects wherein the amount of THC:CBD ranges from about 1.8:1 to about 2.2:1.

A nineteenth aspect which is the composition of the fifteenth through sixteenth aspects wherein the amount of THC:CBD ranges from about 0.4:1 to about 0.6:1

A twentieth aspect which is the composition of any of the fifteenth through nineteenth aspects, where the composition is a beverage.

A twenty-first aspect which is the composition of any of the fifteenth through twentieth aspects wherein the composition is in the form of a nanoemulsion.

A twenty-second aspect which is a method for production of a full spectrum hemp-derived composition, the method comprising obtaining an extract from biomass comprising Cannabis sativa L; separating the extract to obtain a full spectrum distillate; crystallizing the full spectrum distillate to form an isolate and a mother liquor; processing the mother liquor via chromatography to isolate discrete cannabinoids; and blending at least a portion of the mother liquor with discrete cannabinoid isolates to form a blended hemp derived composition having a specific ratio between select cannabinoids.

A twenty-third aspect which is the method of the twenty-second aspect wherein separating the extract comprises distilling the extract.

A twenty-fourth aspect which is the method of any of the twenty-second through twenty-third aspects wherein the isolate comprises greater than 95 wt. % CBD.

A twenty-fifth aspect which is the method of any of the twenty-second through twenty-fourth aspects further comprising emulsifying the full spectrum hemp-derived composition.

A twenty-sixth aspect which is the method of the twenty-fifth aspect wherein emulsifying the full spectrum hemp-derived composition comprises adding one or more additives the full spectrum hemp-derived composition to form a mixture; blending the mixture; and forming an emulsion based on the blending.

A twenty-seventh aspect which is the method of the twenty-sixth aspect wherein the emulsion comprises a nanoemulsion.

A twenty-eighth aspect which is a composition comprising a cannabidiol; and at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof.

A twenty-ninth aspect which is a method for production of a full spectrum hemp-derived composition, the method comprising obtaining an extract from a biomass comprising Cannabis sativa L; separating the extract to obtain a full-spectrum distillate; crystallizing the full spectrum distillate to form an isolate and a mother liquor; and blending at least a portion of the isolate and mother liquor to form a full spectrum hemp-derived composition.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied.

Groups of elements of the periodic table are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens for Group 17 elements, among others.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. While compositions and methods are described in terms of "comprising" various components or steps, the compositions and methods can also "consist essentially of" or "consist of" the various components or steps.

While aspects of the presently disclosed subject matter have been shown and described, modifications thereof can be made by one skilled in the art without departing from the spirit and teachings of the subject matter. The aspects described herein are exemplary only and are not intended to be limiting. Many variations and modifications of the subject matter disclosed herein are possible and are within the scope of the disclosed subject matter. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the aspects of the present invention. The discussion of a reference herein is not an admission that it is prior art to the presently disclosed subject matter, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method for production of a full spectrum hemp-derived composition, the method comprising:
    obtaining an extract from biomass comprising Cannabis sativa L;
    separating the extract to obtain a full spectrum distillate;
    crystallizing the full spectrum distillate to form an isolate and a mother liquor, wherein the isolate is a crystal comprising CBD, and wherein the mother liquor comprises one or more minor cannabinoids;
    separating the isolate from the mother liquid; and
    blending, after separating the isolate from the mother liquor, at least a portion of the isolate and at least a portion of the mother liquor to form a full spectrum hemp-derived composition.

2. The method of claim 1, wherein thefull spectrum hemp-derived composition comprises:
   a cannabidiol;
   at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof, and
   a terpene.

3. The method of claim 2, wherein the at least one compound comprises cannabichromene (CBC), cannabichromenic acid (CBCA), cannabichromevarin (CBCV), cannabichromevarinic acid (CBCVA), cannabicyclol (CBL), cannabicyclolic acid (CBLA) cannabicyclovarin (CBLV), cannabidiol (CBD), cannabidiol monomethylether (CBDM), cannabidiolic acid (CBDA), cannabidiorcol (CBD-C1), cannabidivarin (CBDV), cannabidivarinic acid (CBDVA), cannabielsoic acid B (CBEA-B), cannabielsoin (CBE)
   cannabielsoin acid A (CBEA-A), cannabigerol (CBG), cannabigerol monomethylether (CBGM), cannabigerolic acid (CBGA), cannabigerolic acid monomethylether (CBGAM)
   cannabigerovarin (CBGV), cannabigerovarinic acid (CBGVA), cannabinodiol (CBND), cannabinodivarin (CBVD), cannabinol (CBN), cannabinol methylether (CBNM), cannabinol-C2 (CBN-C2), cannabinol-C4 (CBN-C4), cannabinolic acid (CBNA), cannabiorcool (CBN-C1), cannabivarin (CBV), 10-ethoxy-9-hydroxy-delta-6a-tetrahydrocannabinol, 8,9-dihydroxy-delta-6a-tetrahydrocannabinol, cannabitriol (CBT)
   cannabitriolvarin (CBTV), delta-8-tetrahydrocannabinol (Δ8-THC), delta-8-tetrahydrocannabinolic acid (Δ8-THCA), delta-9-tetrahydrocannabinol (Δ9-THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THCV), delta-9-tetrahydrocannabivarinic acid (THCVA), 10-oxo-delta-6a-tetrahydrocannabinol (OTHC), cannabichromanon (CBCF), cannabifuran (CBF), cannabiglendol, cannabiripsol (CBR), cannbicitran (CBT), dehydrocannabifuran (DCBF), delta-9-cis-tetrahydrocannabinol (cis-THC), trihydroxy-delta-9-tetrahydrocannabinol (triOH-THC) or a combination thereof.

4. The method of claim 2, wherein terpene comprises monoterpenes ($C_{10}$), sesquiterpenes ($C_{15}$), diterpenes ($C_{20}$), triterpenes ($C_{30}$) or a combination thereof.

5. The method of claim 2, wherein the terpene comprises D-limonene, β-carophyllene, myrcene, linalool, α-pinene, nerolidol, humulene, α-bisabolol, camphene, 3-carene, citronellol, cymene, eucalyptol, farnesene, fenchol, geraniol, guaiol, isopropyltoluene, isopulegol, nerolidol, α-ocimene, α-terpinene, γ-terpinene, terpinolene, or a combination thereof.

6. The method of claim 2, wherein the cannabidiol is in the isolate.

7. The method of claim 2, wherein the terpene is a component of the mother liquor.

8. The method of claim 2, wherein the at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols and a combination thereof is a component of the mother liquor.

9. The method of claim 2, wherein the at least one compound comprises delta-9-tetrahydrocannabinol.

10. The method of claim 2, wherein the at least one compound comprises cannabigerol.

11. The method of claim 1, wherein the full spectrum hemp-derived composition comprises a nanoemulsion, and wherein the nanoemulsion comprises:
    a cannabidiol;
    a terpene; and
    an aqueous fluid, wherein the cannabidiol and terpene are in an emulsion in the aqueous fluid.

12. The method of claim 11, further comprising:
    at least one compound selected from the group consisting of cannabichromenes, cannabicyclols, cannabidiols, cannabielsoins, cannabigerols, cannabinols, cannabinodiols, cannabitriols, delta-8-tetrahydrocannabinols, delta-9-tetrahydrocannabinols, or any combination thereof.

13. The method of claim 11, further comprising: delta-9-tetrahydrocannabinol.

14. The method of claim 13, wherein the nanoemulsion is an edible product comprising an amount of delta-9-tetrahydrocannabinol of less than about 0.3 wt. % based on the total weight of the edible product.

15. The method of claim 14, wherein the edible product is a beverage.

16. The method of claim 1, wherein the full spectrum hemp-derived compsition comprsies:
    at least one stereoisomer of tetrahydrocannabinol;
    cannabinodiol; and
    at least one cannabinoid selected from the group consisting of cannabichromenes, cannabicyclols, cannabidiols, cannabielsoins, cannabigerols, cannabinols, cannabinodiols, cannabitriols, and a combination thereof.

17. The method of claim 16, wherein the at least one stereoisomer of tetrahydrocannabinol comprises less than 0.3 wt. % of the composition.

18. The method of claim 16, wherein the amount of THC:CBD ranges from about 0.9:1.0 to about 1.1:1.0.

19. The method of claim 16, wherein the amount of THC:CBD ranges from about 1.8:1 to about 2.2:1.

20. The method of claim 16, wherein the amount of THC:CBD ranges from about 0.4:1 to about 0.6:1.

21. The method of claim 16, where the composition is a beverage.

22. The method of claim 16, wherein the composition is in the form of a nanoemulsion.

23. The method of claim 1, further comprising:
    processing the mother liquor via chromatography to isolate discrete cannabinoids isolates;
    wherein blending at least the portion of the isolate and the mother liquid comprises:
    blending at least a portion of the mother liquor with the discrete cannabinoid isolates to form a blended hemp derived composition having a specific ratio between select cannabinoids.

24. The method of claim 1, wherein separating the extract comprises distilling the extract.

25. The method of claim 1, wherein the isolate comprises greater than 95wt. % CBD.

26. A method for production of a full spectrum hemp-derived composition, the method comprising:
    obtaining an extract from biomass comprising Cannabis sativa L;

separating the extract to obtain a full spectrum distillate;
blending the full spectrum distillate with an additive to form a full spectrum hemp-derived composition, wherein the full spectrum hemp-derived composition comprises at least one stereoisomer of tetrahydrocannabinol, and wherein a concentration of all stereoisomers of tetrahydrocannabinol is less than 0.3 wt. % of the full spectrum hemp-derived composition.

\* \* \* \* \*